(12) United States Patent
Bursalioglu et al.

(10) Patent No.: US 11,497,577 B2
(45) Date of Patent: Nov. 15, 2022

(54) SURGICAL LIGHT, SYSTEM INCLUDING THE SURGICAL LIGHT AND METHOD FOR OPERATING THE SURGICAL LIGHT

(71) Applicant: TRUMPF MEDIZIN SYSTEME GMBH + CO. KG, Saalfeld (DE)

(72) Inventors: Erkan Bursalioglu, Kirchheim (DE); Lena Diedrich, Munich (DE); Andreas Huber, Munich (DE); Matthias Jaeger, Rudolstadt (DE); Verena Kettelhack, Munich (DE); David Lance Ribble, Batesville, IN (US); Clementine Pirio, Vannes (FR)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 469 days.

(21) Appl. No.: 16/693,574

(22) Filed: Nov. 25, 2019

(65) Prior Publication Data

US 2020/0163738 A1   May 28, 2020

(30) Foreign Application Priority Data

Nov. 26, 2018   (EP) .................................... 18208237

(51) Int. Cl.
| | |
|---|---|
| *A61B 90/35* | (2016.01) |
| *A61B 90/00* | (2016.01) |
| *A61B 90/98* | (2016.01) |
| *G06T 7/70* | (2017.01) |
| *G06K 19/07* | (2006.01) |
| *G06T 7/20* | (2017.01) |
| *A61B 17/3201* | (2006.01) |
| *A61B 17/3211* | (2006.01) |
| *F21V 21/108* | (2006.01) |
| *F21W 131/205* | (2006.01) |

(52) U.S. Cl.
CPC .............. *A61B 90/35* (2016.02); *A61B 90/06* (2016.02); *A61B 90/98* (2016.02); *G06K 19/0723* (2013.01); *G06T 7/20* (2013.01); *G06T 7/70* (2017.01); *A61B 17/3201* (2013.01); *A61B 17/3211* (2013.01); *A61B 2090/063* (2016.02); *F21V 21/108* (2013.01); *F21W 2131/205* (2013.01)

(58) Field of Classification Search
None
See application file for complete search history.

(56) References Cited

U.S. PATENT DOCUMENTS

| | | | |
|---|---|---|---|
| 2007/0268133 A1 | 11/2007 | Sanchez et al. | |
| 2009/0267765 A1* | 10/2009 | Greene | ................ G06K 7/0008 340/568.1 |
| 2009/0317002 A1 | 12/2009 | Dein | |
| 2015/0002268 A1 | 1/2015 | Bajema et al. | |
| 2018/0209623 A1 | 7/2018 | Strolin | |
| 2019/0090954 A1* | 3/2019 | Kotian | ................... G16H 70/20 |

FOREIGN PATENT DOCUMENTS

DE   102008039791   3/2010

* cited by examiner

*Primary Examiner* — Thomas S McCormack
(74) *Attorney, Agent, or Firm* — Barnes & Thornburg LLP

(57) ABSTRACT

A surgical light is provided, the surgical light comprising a light head including at least one illuminant configured to generate an illuminated area on a surgical site, and a sensor attached to the light head, wherein the sensor is configured to identify items used in surgery, and the sensor is attached to the light head such that a detection volume of the sensor is directed to the illuminated area.

20 Claims, 2 Drawing Sheets

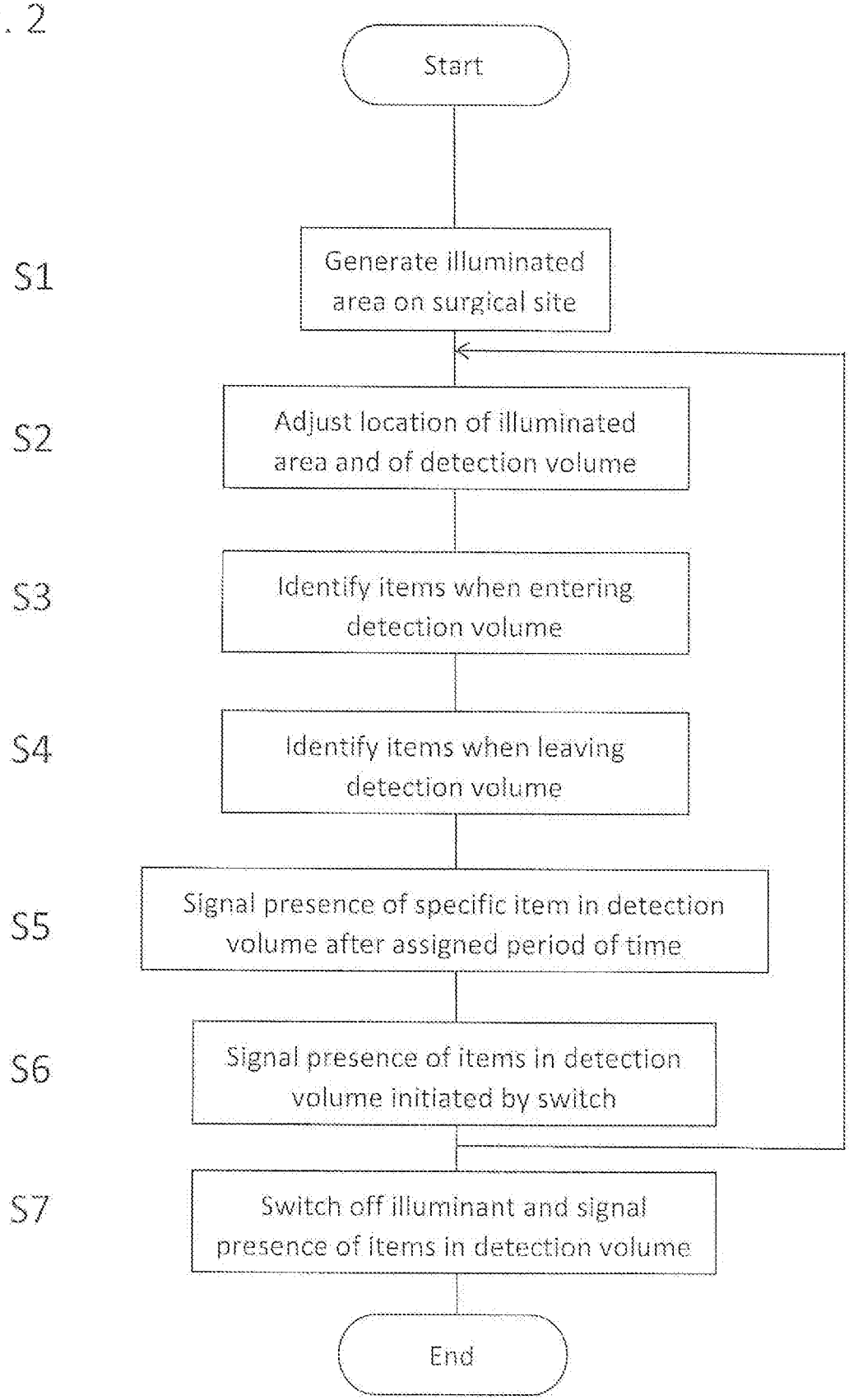

SURGICAL LIGHT, SYSTEM INCLUDING THE SURGICAL LIGHT AND METHOD FOR OPERATING THE SURGICAL LIGHT

CROSS-REFERENCE TO RELATED APPLICATIONS

This application claims the benefit of European Patent Application Serial No. 18208237.0, filed on Nov. 26, 2018, the entire disclosure of which is incorporated herein by reference in its entirety.

TECHNICAL FIELD

The present disclosure relates to a surgical light, a system including the surgical light and a method for operating the surgical light, in particular, to a surgical light provided with additional features.

BACKGROUND

During surgical interventions, there is a risk that instruments, pads or compresses remain in a surgical wound of a patient. Therefore, up to now, in order reduce this risk, e.g., operating room nurses have to identify the instruments and have to count all items being used by a surgeon or by a surgeon assistant. Despite this process, sometimes, some compresses and even instruments stay inside the patient's body after the surgeon has closed the wound. This is dangerous for the patient due to possible post-surgical inflammations and infections. For a hospital, such occurrences lead to a lot of costs due to necessary additional subsequent surgeries.

Therefore, expensive systems have been developed for monitoring the whereabouts of the instruments and objects in an operating room environment. For example, document US 2007/0268133 A1 discloses a system for tracking surgical items in an operating room environment. This system uses several directional antennas with RF transceivers, pointing mechanisms and an ultrasonic transducer for tracking and locating objects and items utilized during surgical procedures in operating room environments.

Therefore, the object underlying the present disclosure is to overcome the above-mentioned disadvantages of unreliable or costly processes and to provide an economic and effective device for tracking items used during surgical procedures.

SUMMARY

The present disclosure includes one or more of the features recited in the appended claims and/or the following features which, alone or in any combination, may comprise patentable subject matter.

According to an aspect of the present disclosure, a surgical light comprises a light head including at least one illuminant configured to generate an illuminated area on a surgical site, and a sensor attached to the light head, wherein the sensor is configured to identify items used in surgery, and the sensor is attached to the light head such that a detection volume of the sensor is directed to the illuminated area.

The detection volume is a volume in which an object can be detected by the sensor. The detection volume can be, e.g., a field of view of a camera or a detection space of a sensor detecting the object within the detection volume by means of specific characteristics of the object.

The surgical light has a central position and it is always focused on the surgical site so that the illuminated area is located on the surgical site. Therefore, the sensor directed to the illuminated area allows an identification of any item, e.g., an instrument, a pad or a compress, which enters into a wound area. Further, the sensor is located in a region close to the surgical site but, nevertheless, does not interfere with operating personnel. Thus, there is no need of sensors which are located far away in order not to disturb the operating personnel but, however, require additional sensors due to a little operating range so that an economic and effective device is provided.

In one implementation of the surgical light, the sensor is configured to cover the illuminated area by the detection volume.

Since the illuminated area is the area where a surgeon performs the surgical intervention, it can be ensured that no undocumented item enters into the surgical wound when the sensor covers the illuminated area by the detection volume.

In a further implementation of the surgical light, the sensor is configured to adapt the detection volume to the illuminated area.

When the detection volume of the sensor is adapted to the illuminated area, any item entering into the surgical wound is detected; however, items outside the surgical wound which are not at risk to enter into the surgical wound are not detected which reduces the amount of data and avoids confusion or misinterpretations.

In a further implementation of the surgical light, the surgical light comprises a controller configured to collaborate with the sensor, and the controller is configured to identify the items when entering into the detection volume, and the controller is configured to identify the items when leaving the detection volume.

By the controller operating in such a manner, a presence of the items in or above the surgical wound can always be comprehended.

In a further implementation of the surgical light, the controller is configured to signal when a specific one of the items does not leave the detection volume after an assigned predetermined period of time.

By this function, it can be determined in an early stage when one of the items is in the surgical wound at a wrong point of time, e.g., an instrument, such as a scalpel, is present in the surgical wound even though it is actually merely used at a beginning of a surgical intervention.

In a further implementation of the surgical light, the controller is configured to signal when the at least one illuminant is switched off and at least one of the items is disposed in the detection volume.

When the detection or check of the items having been disposed in the detection volume is performed upon switching off the light, the validation of removal of all items cannot be forgotten.

In a further implementation of the surgical light, the surgical light comprises a switch configured to induce the controller to determine whether any item is disposed in the detection volume, and the controller is configured to signal when a determination is induced and anyone of the items is disposed in the detection volume.

The switch can be a control button located, e.g., at the light head for being pressed by the operating personnel, however, the switch can also collaborate with, e.g., a speech recognition. Due to the presence of the switch, the determination of the items within the detection volume can be performed at any desired point of time. Therefore, e.g., before closing the surgical wound, the removal of all of the items can be ensured.

In a further implementation of the surgical light, the controller is configured to signal an identification of the at least one of the items disposed in the detection volume.

A provision of the identification of the item facilitates the search of the item in the surgical wound, e.g., a pad in a deep surgical wound.

In a further implementation of the surgical light, the sensor comprises an RFID sensor, and the items are respectively provided with tags identifiable by the RFID sensor.

By providing the sensor with the RFID sensor and equipping the items with tags identifiable by the RFID sensor, the removal of the items can be ensured in a cost-effective and reliable manner.

In another implementation of the surgical light, the sensor comprises a machine vision ability configured to identify the items by means of their optical characteristics.

Due to a provision of the machine vision ability, no specific preparation of the items is necessary and the removal of the items can be ensured in a cost-effective and reliable manner.

According to another aspect of the present disclosure, a system of a surgical light and several tags respectively provided at items used during surgeries is provided.

This system ensures the removal of the items in a cost-effective and reliable manner without disturbing the operation personnel.

According to a further aspect of the present disclosure, a method for operating a surgical light includes the steps: generating an illuminated area by an illuminant in a light head of the surgical light, identifying items used in surgery by a sensor attached to a light head of the surgical light when entering into a detection volume of the sensor; and identifying the items when leaving the detection volume.

By this method, the sensor directed to the illuminated area allows an identification of any item which enters into a wound area. Further, since the sensor is located in a region close to the surgical site but, nevertheless, it does not interfere with operating personnel, there is no need of sensors which are located far away in order not to disturb the operating personnel but, however, require additional sensors due to a little operating range. Therefore, the method can be executed in a cost-effective and reliable manner.

In one implementation of the method, it further comprises the step: simultaneously adjusting a location of the illuminated area and of the detection volume by adjusting the light head.

Due to attaching the sensor to the light head, the sensor can always be directed to the illuminated area on the surgical site even though the light head is adjusted such that it illuminates the surgical site from another position. Therefore, the detection volume is always directed to the illuminated area so that no additional adjustment of the sensor is necessary.

In a further implementation of the method, it further comprises the additional step: signaling presence of any item in the detection volume when the at least one illuminant is switched off.

When the detection of the items disposed in the detection volume is performed upon switching off the illuminant, the validation of removal of all items cannot be forgotten.

In a further implementation of the method, it further comprises the additional steps: initiating a detection of items present in the detection volume by operating a switch, and signaling presence of at least one of the items in the detection volume when the detection is initiated by the switch.

Due to initiating the detection of the items present in the detection volume by the switch, the determination of the items within the detection volume can be performed at any desired point of time. Therefore, e.g., before closing the surgical wound, the removal of all of the items can be ensured.

The invention is hereinafter elucidated by means of an embodiment referring to the attached drawings.

BRIEF DESCRIPTION OF THE DRAWINGS

The detailed description particularly refers to the accompanying figures in which:

FIG. 2 shows a flowchart of a method for operating the surgical light of FIG. 1.

DETAILED DESCRIPTION OF THE DRAWINGS

Figure 1:
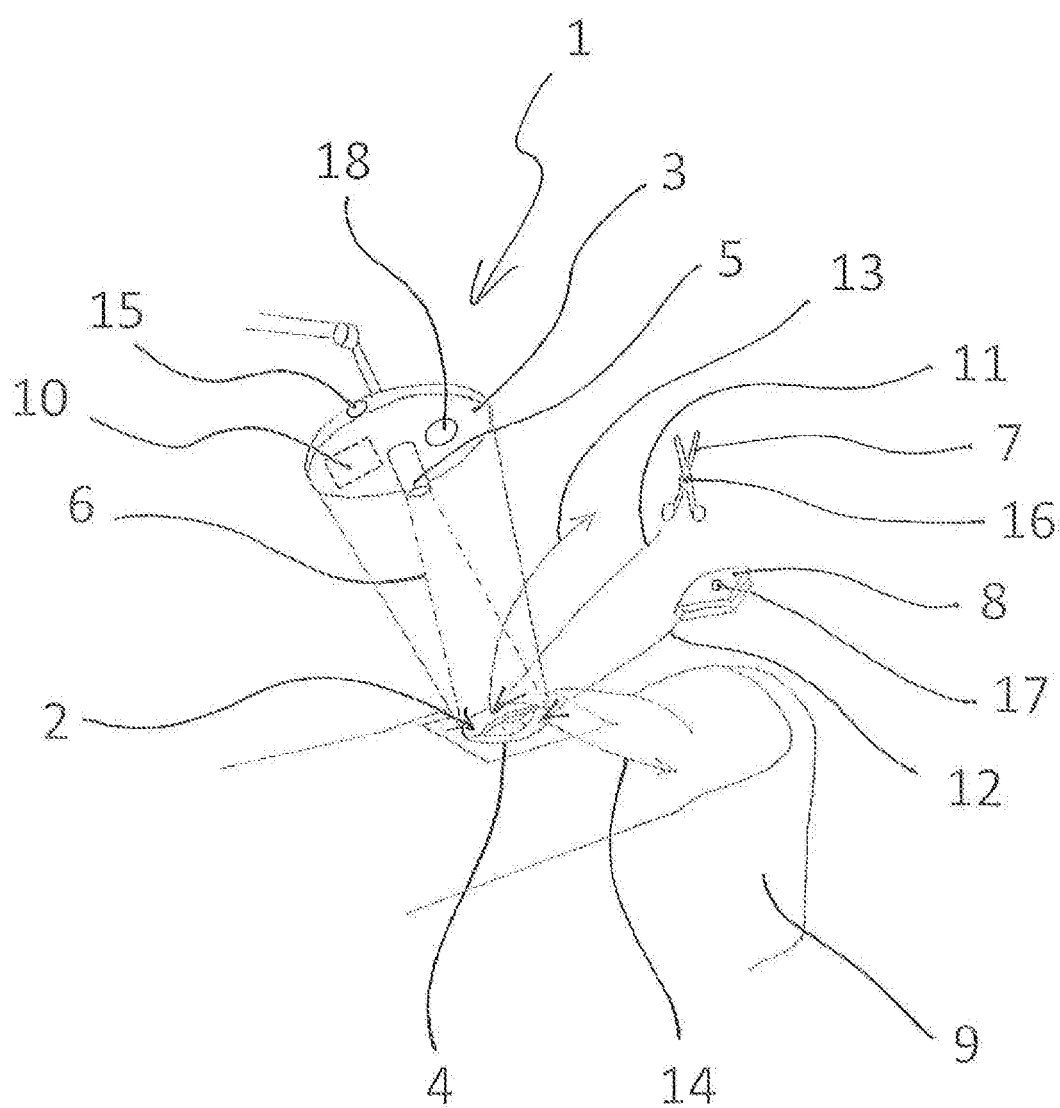
FIG. 1 shows a perspective view of a surgical light according to the present disclosure illuminating a surgical site.

FIG. 1 shows a perspective view of a surgical light 1 illuminating a surgical site 2. The surgical light 1 comprises a light head 3 including at least one illuminant 18 configured to generate an illuminated area 4 on the surgical site 2 and a sensor 5 attached to the light head 3. The sensor 5 is configured to identify items used in surgery, and the sensor 5 is attached to the light head 3 such that a detection volume 6 of the sensor 5 is directed to the illuminated area 4. As items used in surgery, in FIG. 1, a scissor 7 and a compress 8 are depicted. The sensor 5 is a RFID sensor and the items 7, 8 are respectively provided with tags 16, 17 identifiable by the RFID sensor 5. In an alternative embodiment, the sensor 5 comprises a machine vision configured to identify the items 7, 8 by means of their optical characteristics. As the optical characteristics, a shape, dimensions, a color or a reflectance of the surface can be used. Moreover, also a tag provided with optical indicators can be used for being identified by the machine vision. Moreover, alternatively, any other suitable sensor 5 for identifying the items 7, 8 can be used. The surgical light 1 and the tags 16, 17 can be provided as a system.

The surgical site 2 is on a human body lying on an operating table and being covered with a medical drape 9.

The sensor 5 is configured to cover the illuminated area 2 by the detection volume 6. In an alternative embodiment, only a portion of the illuminated area 2, a portion including the surgical wound, for example, is covered by the detection volume 6. Furthermore, the sensor 5 is configured to adapt the detection volume 6 to the illuminated area 4. Thereby, a boundary of the detection volume 6 intersecting the surgical site 2 is adjusted such that it at least almost corresponds to the verge of the illuminated area 4. In an alternative embodiment, the detection volume 6 is not adaptable.

Further, the surgical light 1 comprises a controller 10 collaborating with the sensor 5 and the controller 10 is configured to identify the items 7, 8 when entering into the detection volume 6 as illustrated by arrows 11, 12. The controller 10 is also configured to identify the items 7, 8 when leaving the detection volume 6 as illustrated by arrows 13, 14. As the items 7, 8, also, e.g., a scalpel, pads, etcetera can be identified when entering and leaving the detection volume 6.

The controller 10 is configured to signal when a specific one of the items 7, 8 does not leave the detection volume 6 after an assigned predetermined period of time; in particular, when an instrument as, e.g., the scissor or the scalpel which are only temporarily used remain in the detection volume 6 for a long term. In alternative embodiments, the controller 10 does not have this function.

Furthermore, the controller 10 is configured to signal when the at least one illuminant 18 in the light head 3 is switched off and any item 7, 8 is still disposed in the detection volume 6. The sensor 5 and the controller 10 are supplied via another line and, therefore, despite the switching off of the illuminant 18, the sensor 5 and the controller 10 are still energized, the identification of the items 7, 8 in the detection volume 6 is further performed, and a presence of the items 7, 8 in the detection volume 6 is signaled. The signaling is performed by an audible and visible signal. In alternative embodiments, the signaling is merely performed by one of the signaling means, or the controller 10 is not configured to signal when at least one of the items 7, 8 is disposed in the detection volume 6.

The surgical light 1 comprises a switch in the form of a control button 15 configured to induce the controller 10 to determine whether any item 7, 8 is disposed in the detection volume 6. In this context, the controller 10 is configured to signal when a determination is induced and at least one of the items 7, 8 is disposed in the detection volume 6. In alternative embodiments, the switch can be provided in another manner, e.g. by a device performing speech recognition.

Moreover, the controller 10 is configured to signal an identification of the at least one of the items 7, 8 disposed in the detection volume 6. The controller 10 collaborating with the sensor 5 recognizes the type of the item 7, 8 and signals the identification of the item 7, 8, i.e., a type of item, present in the detection volume 6. This signaling is performed by a display (not shown). In alternative embodiments, the signaling is performed in another manner or the signaling of the identification is omitted.

FIG. 2 shows a flowchart of a method for operating the surgical light 1 of FIG. 1.

In use, in step S1 in FIG. 2, an illuminated area is generated by the illuminant 18 in the light head 3 of the surgical light 1. If necessary, as in step S2, a location of the illuminated area 2 and of the detection volume 6 are simultaneously adjusted by adjusting the light head 3. Then, in step S3, the items 7, 8 used in surgery are identified by the sensor 5 attached to a light head 3 of the surgical light 1 when entering into the detection volume 6 of the sensor 5 and, in step S4, the items 7, 8 are identified when leaving the detection volume 6.

When a specific one of the items 7, 8 does not leave the detection volume 6 after an assigned predetermined period of time, in step S5, the controller 10 signals this state.

For this purpose, there is provided a clock or a timer being started when such an item is entering the detection volume and generates a signal when a predetermined period of time is elapsed.

In step S6, upon actuating the switch by the control button 15 and, thereby, initiating a detection of the items 7, 8 present in the detection volume 6, the presence of at least one of the items 7, 8 in the detection volume 6 is signaled.

When switching off the illuminant 18 of the surgical light 1, in step S7, the presence of at least one of the items 7, 8 in the detection volume 6 is signaled.

Alternatively, not all of the steps S2 and S5 to S7 are to be executed and, nevertheless, a reliable process of the surgery is possible.

While the present disclosure has been illustrated and described in detail in the drawings and the foregoing description, such illustration and description are to be considered illustrative or exemplary and not restrictive. The invention is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

Although this disclosure refers to specific embodiments, it will be understood by those skilled in the art that various changes in form and detail may be made without departing from the subject matter set forth in the accompanying claims.

The invention claimed is:

1. A surgical light comprising
a light head including at least one illuminant configured to generate an illuminated area on a surgical site, and
a sensor attached to the light head,
wherein the sensor is configured to identify items used in surgery, and the sensor is attached to the light head such that a detection volume of the sensor is directed to the illuminated area, wherein the sensor is configured to adapt the detection volume to the illuminated area.

2. The surgical light of claim 1, wherein the sensor is configured to monitor the illuminated area by the detection volume.

3. The surgical light of claim 1, wherein the surgical light comprises a controller configured to collaborate with the sensor, and the controller is configured to identify the items when entering into the detection volume, and the controller is configured to identify the items when leaving the detection volume.

4. The surgical light of claim 3, wherein the controller is configured to signal when a specific one of the items does not leave the detection volume after an assigned predetermined period of time.

5. A surgical light comprising
a light head including at least one illuminant configured to generate an illuminated area on a surgical site, and
a sensor attached to the light head,
wherein the sensor is configured to identify items used in surgery, and the sensor is attached to the light head such that a detection volume of the sensor is directed to the illuminated area,
wherein the surgical light comprises a controller configured to collaborate with the sensor, and the controller is configured to identify the items when entering into the detection volume, and the controller is configured to identify the items when leaving the detection volume,
wherein the controller is configured to signal when a specific one of the items does not leave the detection volume after an assigned predetermined period of time.

6. The surgical light of claim 3, wherein the controller is configured to signal when the at least one illuminant is switched off and at least one of the items is still disposed in the detection volume.

7. The surgical light of claim 3, wherein the surgical light comprises a switch configured to induce the controller to determine whether any item is disposed in the detection volume, and the controller is configured to signal when a determination is induced and anyone of the item is still disposed in the detection volume.

8. The surgical light of claim 6, wherein the controller is configured to signal an identification of the at least one of the items disposed in the detection volume.

9. The surgical light of claim 8, wherein the sensor comprises an RFID sensor, and the items are respectively provided with tags identifiable by the RFID sensor.

10. The surgical light of claim 3, wherein the sensor comprises a machine vision ability configured to identify the items by means of their optical characteristics.

11. The surgical light of claim 1, wherein the sensor comprises an RFID sensor, and the items are respectively provided with tags identifiable by the RFID sensor.

12. The surgical light of claim 1, wherein the sensor comprises a machine vision ability configured to identify the items by means of their optical characteristics.

13. A system comprising
a surgical light including a light head including at least one illuminant configured to generate an illuminated area on a surgical site, and a sensor attached to the light head, and
a plurality of tags on items used during surgeries,
wherein the sensor is configured to identify items used in surgery, and the sensor is attached to the light head such that a detection volume of the sensor is directed to the illuminated area wherein the sensor is configured to adapt the detection volume to the illuminated area.

14. A method for operating a surgical light, including the steps:
generating an illuminated area by an illuminant in a light head of the surgical light;
identifying items used in surgery by a sensor attached to the light head of the surgical light when entering into a detection volume of the sensor;
adapting the detection volume of the sensor to correspond to the illuminated area; and
identifying the items when leaving the detection volume.

15. The method of claim 14, including the additional step:
simultaneously adjusting a location of the illuminated area and of the detection volume by adjusting the light head.

16. A method for operating a surgical light, including the steps:
generating an illuminated area by an illuminant in a light head of the surgical light;
identifying items used in surgery by a sensor attached to the light head of the surgical light when entering into a detection volume of the sensor;
identifying the items when leaving the detection volume,
simultaneously adjusting a location of the illuminated area and of the detection volume by adjusting the light head, and
signaling presence of any item in the detection volume when the illuminant of the surgical light is switched off.

17. The method of claim 16, including the additional steps:
initiating a detection of items present in the detection volume by operating a switch; and
signaling presence of at least one of the items in the detection volume when the detection is initiated by the switch.

18. The method of claim 14, including the additional step:
signaling presence of any item in the detection volume when the illuminant of the surgical light is switched off.

19. The surgical light of claim 5, wherein the controller is configured to signal when the at least one illuminant is switched off and at least one of the items is still disposed in the detection volume.

20. The surgical light of claim 5, wherein the surgical light comprises a switch configured to induce the controller to determine whether any item is disposed in the detection volume, and the controller is configured to signal when a determination is induced and anyone of the item is still disposed in the detection volume.

* * * * *